United States Patent [19]

Franke et al.

[11] Patent Number: 5,131,946

[45] Date of Patent: Jul. 21, 1992

[54] ANILINO IMINOAZOLES AND IMINOAZINES, PROCESS FOR THEIR PREPARATION AND THEIR USES

[75] Inventors: Wilfried Franke; Friedhelm Blume; Friedrich Arndt; Richard Rees, all of Berlin, Fed. Rep. of Germany

[73] Assignee: Schering Aktiengesellschaft, Fed. Rep. of Germany

[21] Appl. No.: 215,600

[22] Filed: Jul. 6, 1988

[30] Foreign Application Priority Data

Jul. 7, 1987 [DE] Fed. Rep. of Germany ....... 3722827

[51] Int. Cl.$^5$ .................... A01N 43/84; C07D 515/04
[52] U.S. Cl. ........................................... 71/90; 71/91; 544/47; 546/114; 548/161
[58] Field of Search .................... 548/161, 222; 71/88, 71/90, 91; 546/114; 544/47

[56] References Cited

PUBLICATIONS

Ayra, et al. *Ch. Ab.* 87: 5887 (1977).
"Synthesis of New Heterocycles: Part XVI*—Synthesis of Thiazolo[3,4-]pyridines, ..." by V. P. Arya et al., Indian Journal of Chemistry, vol. 14B, Oct. 1976, pp. 770–772.

*Primary Examiner*—Mary C. Lee
*Assistant Examiner*—Jacqueline Haley
*Attorney, Agent, or Firm*—Ostrolenk, Faber, Gerb & Soffen

[57] ABSTRACT

The invention relates to new anilino iminoazoles and iminoazines of general formula I

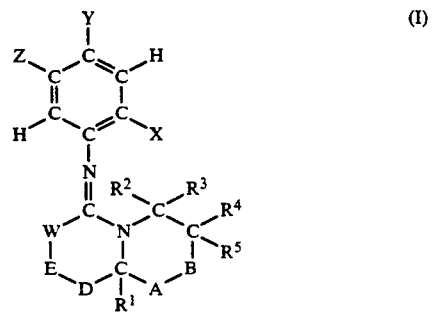

in which A, B, D, E, W, X, Y, Z, $R^1$, $R^2$, $R^3$, $R^4$ and $R^5$ have the meanings given in the description, processes for their preparation and their use as herbicides.

21 Claims, No Drawings

ANILINO IMINOAZOLES AND IMINOAZINES, PROCESS FOR THEIR PREPARATION AND THEIR USES

DESCRIPTION

This invention relates to new anilino iminoazoles and iminoazines, processes for their preparation and their use as herbicides.

It is known that phenyliminodiazole compounds possess herbicidal activity (DE OS 36 28 583). However the herbicidal activity of the known compounds is not sufficient or selectivity problems can occur in important crops.

The object of the present invention is to make new compounds that do not show the disadvantages of the known compounds and have improved biological properties.

It has now been found that anilino iminoazoles and iminoazines of general formula I

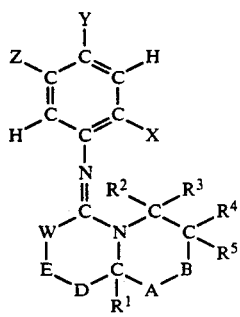

in which
- A is the group $(CR^6R^7)_n$,
- B is oxygen or the group $CR^8R^9$,
- D is the group $(CR^{10}R^{11})_n$,
- E is the group $CR^{12}R^{13}$,
- W is oxygen or the group $S(O)_m$,
- X and Y, independently of each other, are hydrogen or halogen,
- Z is hydrogen, halogen or trifluoromethyl or one of the groups $-OR^{14}$, $-SR^{14}$, $-NR_2^{14}$ or $-CO_2R^{15}$.
- $R^1$ is hydrogen, $C_1$-$C_2$-alkyl or halo-$C_1$-$C_2$-alkyl, $R^2$, $R^3$, $R^4$, $R^5$, $R^6$, $R^7$, $R^8$, $R^9$, $R^{10}$, $R^{11}$, $R^{12}$ and $R^{13}$, independently of each other, are hydrogen, $C_1$-$C_4$-alkyl, halo-$C_1$-$C_4$-alkyl, $C_1$-$C_4$-alkoxy, $C_1$-$C_4$-alkylthio, halo-$C_1$-$C_4$-alkoxy or halo-$C_1$-$C_4$-alkylthio, or
- $R^2$, $R^3$, $R^4$, $R^5$, $R^6$, $R^7$, $R^8$, $R^9$, $R^{10}$, $R^{11}$, $R^{12}$ and $R^{13}$, optionally together are one or more rings or alkylidene groups.
- $R^{14}$ is hydrogen, a $C_1$-$C_{12}$-alkyl, $C_3$-$C_8$-cycloalkyl, $C_2$-$C_6$-alkenyl or $C_3$-$C_8$-alkynyl group, each of which is optionally substituted by one or more halogen atoms, carboxy-$C_1$-$C_8$-alkyl, a $C_1$-$C_4$-alkoxy-, $C_2$-$C_4$-alkenyloxy- or $C_3$-$C_4$-alkynyloxy-carbonyl-$C_1$-$C_8$-alkyl group, $C_1$-$C_8$-alkoxy-$C_1$-$C_8$-alkyl, $C_1$-$C_4$-alkylsulphonyl, optionally substituted by one or more halogen atoms, phenylsulphonyl, optionally substituted, one or more times, by the same or different halogen, $C_1$-$C_4$-alkyl, halo-$C_1$-$C_4$-alkyl, nitro, $C_1$-$C_4$-alkoxy or halo-$C_1$-$C_4$-alkoxy, $C_1$-$C_4$-alkyl, substituted by a saturated or unsaturated heterocycle, or phenyl or phenyl-$C_1$-$C_4$-alkyl, both of which are optionally substituted one or more times by the same or different halogen, $C_1$-$C_4$-alkyl, halo-$C_1$-$C_4$-alkyl, nitro, $C_1$-$C_4$-alkoxy or halo-$C_1$-$C_4$-alkoxy.
- $R^{15}$ is hydrogen, a $C_1$-$C_6$-alkyl, $C_2$-$C_6$-alkenyl or $C_3$-$C_6$-alkynyl group each of which is optionally substituted by one or more halogen atoms,
- n is 0 or 1, and
- m is 0, 1 or 2, and their salts with inorganic and organic acids, show an interesting herbicidal activity.

The compounds of general formula I can optionally exist in various enantiomeric, diastereomeric or geometric forms and these are within the scope of this invention.

The term "halogen" means fluorine, chlorine, bromine and iodine.

The term "haloalkyl" means that one or more hydrogen atoms of the alkyl group are replaced by halogen.

Examples of saturated and unsaturated heterocycles are tetrahydrofuran, tetrahydrothiophene, pyrrolidine piperidine morpholine pyridine and pyrrole.

The compounds of the invention of general formula I can be prepared by

A) cyclising a compound of general formula II

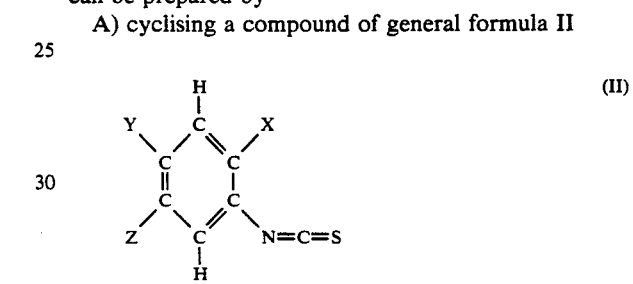

in which X, Y and Z have the meanings given under general formula I, in a one pot process, under acid conditions, with a compound of general formula III

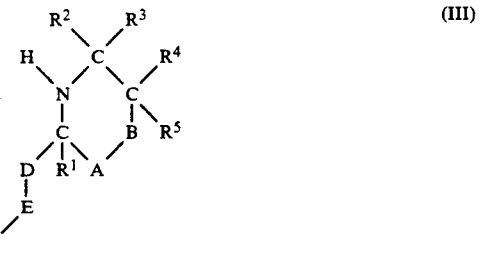

in which A, B, D, E, $R^1$, $R^2$, $R^3$, $R^4$ and $R^5$ have the meanings given under general formula I, B) in the case when W in general formula I is oxygen, reacting a compound of general formula II

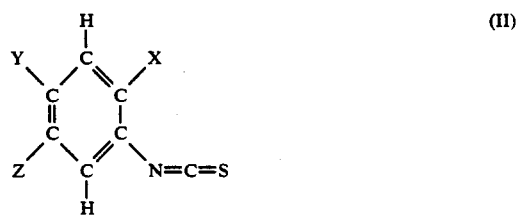

in which X, Y and Z have the meanings given under general formula I, in a one pot process in a suitable solvent, with a compound of general formula III

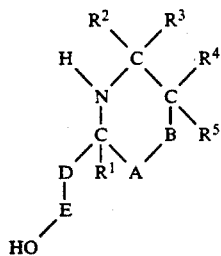

(III)

in which A, B, D, E, $R^1$, $R^2$, $R^3$, $R^4$ and $R^5$ have the meanings given under general formula I, C) cyclising a thiourea of general formula IV

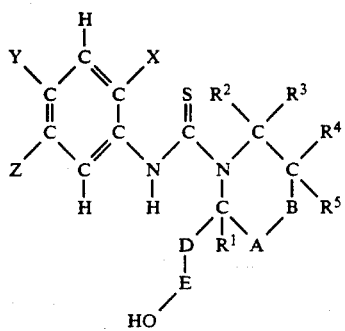

(IV)

in which A, B, D, E, X, Y, Z, $R^1$, $R^2$, $R^3$, $R^4$ and $R^5$ have the meanings given under general formula I, under acid conditions, or optionally in a suitable solvent, under neutral conditions, D) reacting a compound of general formula V

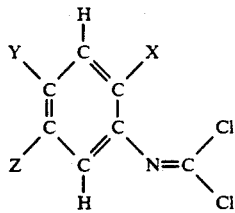

(V)

in which X, Y and Z have the meanings given under general formula I, with a compound of general formula VI

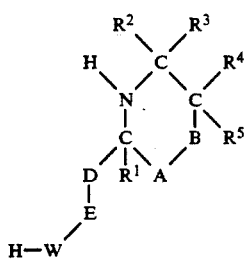

(VI)

in which A, B, D, E, $R^1$, $R^2$, $R^3$, $R^4$ and $R^5$ have the meanings given under general formula I, in a suitable solvent, under basic conditions, E) in the case when Z in general formula I is —$OR^{14}$ or —$SR^{14}$, —$NR_2^{14}$, except $R^{14}$ is not hydrogen, phenyl or substituted phenyl, reacting a compound of general formula VII

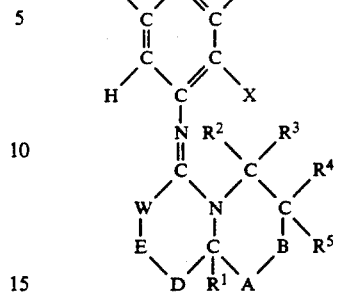

(VII)

in which A, B, D, E, W, X, Y, $R^1$, $R^2$, $R^3$, $R^4$ and $R^5$ have the meanings given under general formula I and $Z^1$ is —OH, —SH or $NH_2$, with a compound of general formula VIII $R^{14}$—G (VIII)

in which G is halogen, p-toluenesulphonyloxy or methanesulphonyloxy or the group $R^{14}O$—$SO_2$—O— and $R^{14}$ has the meaning given under general formula I, except hydrogen, phenyl or substituted phenyl, optionally with the addition of a base, and F) in the case when Z in general formula I is —OH, a compound of general formula IX

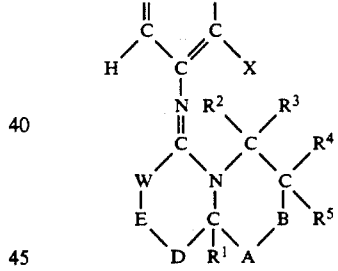

(IX)

in which A, B, D, E, W, X, Y, $R^1$, $R^2$, $R^3$, $R^4$ and $R^5$ have the meanings given under general formula I and $Z^2$ is $C_1$-$C_{14}$-alkoxy or $C_3$-$C_8$-cycloalkoxy, is subjected to an ether cleavage, with a strong mineral acid, or G) in the case when Z in general formula I is —OH, —SH or $NH_2$, a compound of general formula X

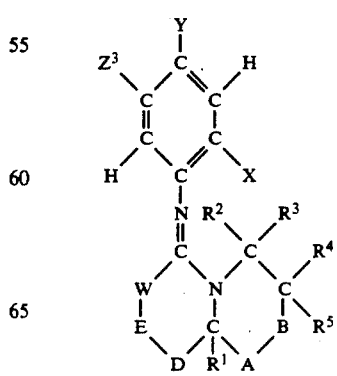

(X)

in which A, B, D, E, W, X. Y, $R^1$, $R^2$, $R^3$, $R^4$ and $R^5$ have the meanings given under general formula I and $Z^3$ is —OR, —SR or $NR_2$, in which R is $C_1$-$C_4$-alkylsulphonyl, optionally substituted by one or more halogens, or is phenylsulphonyl, optionally substituted by $C_1$-$C_3$-alkyl or halogen, is hydrolysed under basic conditions.

Where the preparation of the starting materials is not described, they are either known or can be prepared according to known methods.

Process variant A is suitably carried out by reacting the starting compounds of general formulae II and III in an organic solvent, such as for example diethyl ether, tetrahydrofuran, dioxane, methanol or ethanol, optionally with the addition of catalytic amounts of an amine, such as for example triethylamine, over a long period such as for example 0.5 to 10 hours, at a temperature of 20° C. up to the boiling point of the particular solvent. Then the solvent is separated and the residue heated under reflux with a strong mineral acid, such as for example hydrochloric acid, hydrobromic acid or even sulphuric acid, for 0.5 to 10 hours. After neutralising with for example caustic soda, work-up is carried out in the usual manner. The salts of the compounds are obtained if the work up is carried out in the usual manner before neutralisation.

The process variant B is suitably carried out by reacting the starting compounds of of general formulae II and III in an organic solvent as given under process A, optionally with the addition of catalytic amounts of an amine, such as for example triethylamine, over a long period, such as for example 0.5 to 15 hours, at a temperature of 20° C. up to the boiling point, and generally at the boiling point of the particular solvent.

The process variant C is suitably carried out by heating under reflux the thioureas of general formula IV with a strong mineral acid, such as for example hydrochloric acid, hydrobromic acid or even sulphuric acid, for 0.5 to 10 hours. The cyclisation can optionally also be carried out under neutral conditions in which the ureas of general formula IV are heated in a solvent given under process A over a long period such as for example 0.5 to 15 hours. The temperature can vary between 50° C. and the boiling point of the particular solvent.

The process variant D is suitably carried out by reacting compounds of general formula V with compounds of general formula VI in a suitable solvent, in the presence of bases, at a temperature between 0° C. and 100° C., preferably between 10° C. and 50° C. As solvents all inert organic solvents can be considered. Examples include hydrocarbons, such as for example toluene, chlorinated hydrocarbons, such as for example methylene chloride, chloroform or carbon tetrachloride, and ethers, such as for example diethyl ether, dioxane or tetrahydrofuran. As bases there can be used all inorganic and organic bases, but preferably organic bases, such as for example triethylamine or pyridine.

The process variant E is suitably carried out by reacting the starting materials in a suitable solvent with the addition or an inorganic or organic base at a temperature of between 0° C. and 150° C., preferably at the reflux temperature of the solvent. The reaction can also be carried out in a two phase system with the addition of a phase transfer catalyst.

As bases there can be used alkali and alkaline earth metal hydroxides and alcoholates, alkali metal hydrides, alkali and alkaline earth metal carbonates and hydrogen carbonates, tertiary aliphatic and aromatic amines, as well as heterocyclic bases. Examples are sodium and potassium hydroxide, sodium methanolate, sodium hydride, sodium and potassium carbonate, sodium and potassium hydrogen carbonate, triethylamine and pyridine.

Examples of solvents are hydrocarbons, such as for example toluene, chlorinated hydrocarbons, such as for example methylene chloride or chloroform, ethers such as for example diethyl ether or tetrahydrofuran, alcohols, such as for example methanol or ethanol, ketones, such as for example acetone or butanone, amides, such as for example dimethylformamide and also sulphoxide, such as for example dimethyl sulphoxide.

Process variant F can be suitably carried out by heating the phenol ether with a strong mineral acid. Examples of acids are hydrobromic acid or hydroiodic acid. Generally the acid also serves as solvent. Also organic acids, such as for example acetic acid can be used. The reaction is carried out at a temperature of 50° C. to the boiling point of the respective solvent, generally at the boiling point of the solvent.

Process variant G is suitably carried by hydrolysing the starting material with an aqueous or aqueous alcoholic alkali or alkaline earth metal hydroxide, alkali or alkaline earth metal carbonate or hydrogen carbonate solution, at a temperature of 20° C. to 150° C. to give the corresponding derivatives.

The work up of compounds of the invention prepared by process variants A to G can be carried out in the usual manner. Purification or optional separation of the resulting isomeric compounds can be carried out by recrystallisation or column chromatography.

The active substances of the invention show a good herbicidal activity against broad leaved weeds and grasses. A selective use of the compounds of the invention in various crops is possible for example in rape, beet, soya beans, cotton, rice, barley, wheat and other cereals. Individual active substances are particularly suitable as selective herbicides in beet, cotton, soya and cereals. However the compounds can be used for control of weeds in permanent crops, such as for example forestry, ornamental trees, fruit, vine, citrus, nut, banana, coffee, tea, rubber, oil palm, cocoa, berry fruit and hop plantations and for the selective control of weeds in annual crops. The active ingredients of the invention can also be used as defoliants, dessicants and weed killers.

The compounds of the invention can used for example against the following plant species:

Dicotyledonous weeds of the species Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.

Monocotyledonous weeds of the species Avena, Alopecurus, Echinochloa, Setaria, Panicum, Digitaria, Poa, Eleusine, Brachiaria, Lolium, Bromus, Cyperus, Agropyron, Sagittaria, Monocharia, Fimbristylis, Eleocharis, Ischaemum and Apera.

The rates of use vary depending on the manner of pre- and postemergent use between 0.05 and 5 kg/ha.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 34, No. 5 (1986) under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

Suitable mixture partners may include phospholipids, e.g. phosphatidylcholine, hydrated phosphatidylcholines phosphatidylethanolamine, N-acyl-phosphatidylethanolamines, phosphatidylinositol, phosphatidylserine, lysolecithin or phosphatidylglycerol.

The designated active ingredients or their mixtures can suitable be used for example, as powders dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example the compositions can contain about 10 to 90 percent by weight active ingredients, and about 90 to 10 percent by weight liquid or solid carriers as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

A) Wettable Powder
1) 25 percent by weight active ingredient
   60 percent by weight kaolin
   10 percent by weight silicic acid
   5 percent by weight of a mixture of calcium lignosulphonate and the sodium salt of N-methyl-N-oleyltaurine
2) 40 percent by weight active ingredient
   25 percent by weight bentonite
   25 percent by weight colloidal silicic acid
   10 percent by weight of a mixture of calcium lignosulphonate and alkylphenyl polyglycol ether B) Paste
   45 percent by weight active ingredient
   5 percent by weight sodium aluminium silicate
   15 percent by weight cetyl polyglycol ether with 8 mol of ethylene oxide
   2 percent by weight spindle oil
   10 percent by weight polyethylene glycol
   23 percent by weight water C) Emulsifiable Concentrate
   25 percent by weight active ingredient
   15 percent by weight cyclohexanone
   55 percent by weight xylene
   5 percent by weight of a mixture of calcium dodecylbenzenesulphonate and nonylphenol-polyoxyethylene.

The following examples illustrate the preparation of compounds according to the invention.

EXAMPLE 1

3-(4-Chloro-2-fluoro-5-methylsulphonyloxy-phenylimino)-tetrahydro-1H,3H-pyrrolo[1,2-c]thiazole (process A)

10 g 2-(Hydroxymethyl)pyrrolidine and 27.6 g 4-chloro-2-fluoro-5-methylsulphonyloxyphenyl isothiocyanate were heated under reflux for 4 hours in 200 ml dioxane. The solvent was removed and the residue heated with 50 ml 48% hydrobromic acid. After cooling, the reaction solution was added to an ice/water mixture, neutralised with 40% caustic soda and extracted with methylene chloride. After drying and concentrating, the crude product was purified by column chromatography (silica gel, eluent; hexane/ethyl acetate).

Yield: 31 g=87% of theory.
Mp: 68°-70° C.

EXAMPLE 2

3-(4-Chloro-2-fluoro-5-methoxyphenylimino)-1-methylhexahydro-3H-oxazolo[3,4-a]pyridine (Process B)

14.3 g 2-(1-Hydroxyethyl)piperidine in 25 ml dioxane were treated at room temperature with 23.9 g 4-chloro-2-fluoromethoxyphenyl isothiocyanate and heated for 4 hours under reflux. The solvent was removed and the crude product purified by column choromatography (silica gel, eluent: hexane/ethyl acetate).

Yield: 34.9 g=41% of theory,
Mp: Viscous oil,

EXAMPLE 3

3-(2-Chlorophenylimino)hexahydro-3H-thiazolo[3,4-a]pyridine (process C)

1 g 1-(2-Chlorophenylthiocarbamoyl)-2-hydroxymethylpiperidine in 20 ml 48% hydrobromic acid was heated under reflux for 2 hours. The mixture was then neutralised under cooling with 2N caustic soda, extracted with methylene chloride, the extracts dried over magnesium sulphate and the solvent distilled. The residue was recrystallised from diisopropyl ether.

Yield: 0.64 g=68% of theory, Mp: 110° C.,
The starting material was prepared as follows:
1-(2-Chlorophenylthiocarbamoyl)-2-hydroxymethyl-piperidine.

3.4 g 2-Hydroxymethylpiperidine in 50 ml absolute tetrahydrofuran was treated with 1 drop of triethylamine and 5 g 2-chlorophenyl isothiocyanate. After 12 hours at room temperature, the reaction solution was cooled in an ice bath. The crystals were suction filtered and recrystallised from ethyl acetate.

Yield: 3.5 g=45% of theory.
Mp: 148° C.

EXAMPLE 4

3-Phenyliminohexahydro-3H-oxazolo[3,4-a]pyridine (Process D)

3 g Phenyl isocyanide dichloride in 10 ml methylene chloride was treated at room temperature with a solution of 5.4 ml triethylamine and 1.7 g 2-hydroxymethylpiperidine in 20 ml methylene chloride. After 12 hours at room temperature, the mixture was washed with water, the organic phase was dried over magnesium sulphate, the solvent was distilled and the residue recrystallised from diisopropyl ether.

Yield: 1.7 g=52% of theory.
Mp: 58° C.

EXAMPLE 5

3-(4-Chloro-2-fluoro-5-isopropoxyphenylimino)-1-methylhexahydro-3H-oxazolo[3,4-a]pyridine (process E)

3.5 g 3-(4-Chloro-2-fluoro-5-hydroxyphenylimino)-1-methylhexahydro-3H-oxazolo[3,4-a]pyridine and 6.6 g potassium carbonate in 40 ml acetone was treated at room temperature with 3.1 g 2-bromopropane and heated under reflux for 6 hours. It was then treated again with 3.1 g 2-bromopropane and heated under reflux for 6 hours. After cooling the mixture was filtered, the filtrate concentrated and the residue purified by column chromatography (silica gel, eluent; hexane/ethyl acetate).

Yield: 3.7 g=93% of theory.
Mp: Oil ($n_D^{40}$ 1.5502).

EXAMPLE 6

3-(4-Chloro-2-fluoro-5-hydroxyphenylimino)-1-methylhexahydro-3H-oxazolo[3,4-a]pyridine (process F)

14.4 g 3-(4-Chloro-2-fluoro-5-methoxyphenylimino)-1-methylhexahydro-3H-oxazolo[3,4-a]pyridine was heated under reflux with 25 ml 48% hydrobromic acid for 5 hours. After cooling it was neutralised with 40% caustic soda and extracted with ethyl acetate. The organic phase was dried over magnesium sulphate, concentrated and the residue recrystallised from petroleum ether.

Yield 8 g=58% of theory.
Mp: 144° C.

EXAMPLE 7

3-(4-Chloro-2-fluoro-5-hydroxyphenylimino)tetrahydro-1H,3H-pyrrolo[1,2-c]thiazole (Process G)

22 g 3-(4-Chloro-2-fluoro-5-methylsulphonyloxyphenylimino)-tetrahydro-1H,3H-pyrrolo[1,2-c]thiazole in 400 ml ethanol was treated with 400 ml 2 N caustic soda and stirred at 40° C. for 4 hours. With ice cooling it was then neutralised with 10% hydrochloric acid and extracted with methylene chloride. After drying over magnesium sulphate and concentrating, the residue was recrystallised from isopropanol.

Yield: 1.58 g=91% of theory.
Mp: 158°-161° C.

In a similar manner to Examples 1 to 7 the following compounds of the invention were prepared were prepared.

| Example No | $R^1$ | $R^2$ | $R^3$ | $R^4$ | $R^5$ | A | B | D | E | W | X | Y | Z | Mp. (°C.) or $n_D$ |
|---|---|---|---|---|---|---|---|---|---|---|---|---|---|---|
| 8 | H | H | H | H | H | $CH_2$ | $CH_2$ | $CH_2$ | $CH_2$ | S | F | Cl | $OCH_3$ | 79–81 |
| 9 | H | H | H | H | H | $CH_2$ | $CH_2$ | — | $CH_2$ | S | F | Cl | $OCH_3$ | oil |
| 10 | H | H | H | H | H | — | $CH_2$ | — | $CH_2$ | S | F | Cl | $OCH_3$ | 118 |
| 11 | H | H | H | H | H | — | $CH_2$ | — | $CH_2$ | S | F | Cl | OH | 58–161 |
| 12 | H | H | H | H | H | — | $CH_2$ | — | $CH_2$ | S | F | Cl | $OCH(CH_3)_2$ | 82–84 |
| 13 | H | H | H | H | H | $CH_2$ | $CH_2$ | — | $CH_2$ | O | F | Cl | OH | 160 |
| 14 | H | H | H | H | H | $CH_2$ | $CH_2$ | — | $CH_2$ | O | F | Cl | $OSO_2CH_3$ | 96–98 |
| 15 | H | H | H | H | H | $CH_2$ | $CH_2$ | — | $CH_2$ | O | F | Cl | $OCH(CH_3)_2$ | $n_D^{22}$ = 1.5618 |
| 16 | H | H | H | H | H | $CH_2$ | $CH_2$ | — | $CHCH_3$ | O | F | Cl | $OCH_2CO_2C_2H_5$ | 95 |
| 17 | H | H | H | H | H | $CH_2$ | $CH_2$ | — | $CHCH_2CH_3$ | O | F | Cl | OH | 162 |
| 18 | H | H | H | H | H | $CH_2$ | $CH_2$ | — | $CHCH_2CH_3$ | O | F | Cl | $OCH_3$ | oil |
| 19 | H | $CH_3$ | H | H | H | $CH_2$ | $CH_2$ | — | $CHCH_3$ | O | F | Cl | $OCH_3$ | 78 |
| 20 | H | H | H | H | H | $CH_2$ | $CH_2$ | — | $CH_2$ | S | F | Cl | OH | 138–140 |
| 21 | H | H | H | H | H | — | $CH_2$ | — | $CH_2$ | S | F | Cl | $OCH(CH_3)C_2H_5$ | 72–74 |
| 22 | H | H | H | H | H | $CH_2$ | $CH_2$ | — | $CH_2$ | S | F | Cl | $OSO_2CH_3$ | 96–98 |
| 23 | H | H | H | H | H | $CH_2$ | $CH_2$ | — | $CH_2$ | S | F | Cl | $OCH(CH_3)C_2H_5$ | 55–58 |
| 24 | H | H | H | H | H | $CH_2$ | $CH_2$ | $CH_2$ | $CH_2$ | S | F | Cl | $OSO_2CH_3$ | 100 |
| 25 | H | H | H | H | H | $CH_2$ | $CH_2$ | $CH_2$ | $CH_2$ | S | F | Cl | OH | 138 |
| 26 | H | H | H | H | H | $CH_2$ | $CH_2$ | $CH_2$ | $CH_2$ | S | F | Cl | OH | >220 (× HCl) |
| 27 | H | H | H | H | H | $CH_2$ | $CH_2$ | — | $CH_2$ | S | F | Cl | $OCH_2CO_2C_2H_5$ | 93 |
| 28 | H | H | H | H | H | $CH_2$ | $CH_2$ | — | $CH_2$ | S | F | Cl | $OCH_2CH=CH_2$ | $n_D^{42}$ = 1.596 |
| 29 | H | H | H | H | H | $CH_2$ | $CH_2$ | — | $CH_2$ | S | F | Cl | $OCH_2C\equiv CH$ | 77–79 |
| 30 | H | H | H | H | H | $CH_2$ | $CH_2$ | — | $C(CH_3)_2$ | O | F | Cl | $OCH_3$ | oil |
| 31 | H | H | H | H | H | $CH_2$ | $CH_2$ | — | $CH_2$ | O | Cl | H | H | 45–48 |
| 32 | H | H | H | H | H | — | $CH_2$ | — | $CH_2$ | S | F | Cl | $OCH_2CH=CH_2$ | |
| 33 | H | H | H | H | H | $CH_2$ | $CH_2$ | — | $CH_2$ | S | F | Cl | $OCH(CH_3)_2$ | $n_D^{42}$ = 1.580 |
| 34 | H | H | H | $CH_3$ | $CH_3$ | — | $CH_2$ | — | $CH_2$ | S | F | Cl | $OCH_3$ | oil |
| 35 | H | H | H | H | H | — | $CH_2$ | — | $CH_2$ | S | F | Cl | $OCH_2C\equiv CH$ | 105 |
| 36 | H | H | H | H | H | — | $CH_2$ | — | $CH_2$ | S | F | Cl | $OCH_2CO_2C_2H_5$ | oil |
| 37 | H | H | H | H | H | — | $CH_2$ | — | $CH_2$ | O | F | Cl | $OCH(CH_3)_2$ | oil |
| 38 | H | H | H | H | H | — | $CH_2$ | — | $CH_2$ | O | F | Cl | $O(CH_2)_3CH_3$ | oil |
| 39 | H | H | H | H | H | — | $CH_2$ | — | $CH_2$ | O | F | Cl | $OCH_2CO_2C_2H_5$ | oil |
| 40 | H | H | H | H | H | — | $CH_2$ | — | $CH_2$ | S | F | Cl | $CO_2C_2H_5$ | $n_D^{20}$ = 1.5978 |
| 41 | H | H | H | H | H | $CH_2$ | $CH_2$ | — | $CH_2$ | S | F | Cl | $CO_2C_2H_5$ | 51 |
| 42 | H | H | H | H | H | $CH_2$ | $CH_2$ | — | $CH_2$ | S | Cl | Cl | H | 61 |
| 43 | H | H | H | H | H | $CH_2$ | $CH_2$ | — | $CH_2$ | S | H | H | $CF_3$ | 83 |

-continued

| Example No | $R^1$ | $R^2$ | $R^3$ | $R^4$ | $R^5$ | A | B | D | E | W | X | Y | Z | Mp. (°C.) or $n_D$ |
|---|---|---|---|---|---|---|---|---|---|---|---|---|---|---|
| 44 | H | H | H | H | H | $CH_2$ | $CH_2$ | — | $CH_2$ | S | F | Cl | $CO_2H$ | 96 (dec) |
| 45 | H | H | H | H | H | — | $CH_2$ | — | $CH_2$ | S | F | Cl | $CO_2H$ | 97 (dec) |
| 46 | H | H | H | H | H | $CH_2$ | $CH_2$ | — | $CH_2$ | S | F | Cl | $CO_2CH_3$ | $n_D^{20} = 1.6076$ |
| 47 | H | H | H | H | H | — | $CH_2$ | — | $CH_2$ | S | F | Cl | $CO_2CH_3$ | $n_D^{20} = 1.6171$ |
| 48 | H | H | H | H | H | $CH_2$ | $CH_2$ | — | $CH_2$ | S | F | Cl | $CO_2CH_2C\equiv CH$ | $n_D^{20} = 1.6081$ |
| 49 | H | H | H | H | H | — | $CH_2$ | — | $CH_2$ | S | F | Cl | $CO_2CH_2C\equiv CH$ | 86 |
| 50 | H | H | H | H | H | $CH_2$ | $CH_2$ | — | $CH_2$ | S | F | Cl | $CO_2(CH_2)_4CH_3$ | $n_D^{20} = 1.5753$ |
| 51 | H | H | H | H | H | — | $CH_2$ | — | $CH_2$ | S | F | Cl | $CO_2(CH_2)_4CH_3$ | $n_D^{20} = 1.5826$ |
| 52 | H | H | H | H | H | $CH_2$ | $CH_2$ | — | $CH_2$ | S | F | Cl | $SCH_2CO_2-\langle\text{cyclopentyl}\rangle$ | gum |
| 53 | H | H | H | H | H | $CH_2$ | $CH_2$ | — | $CH_2$ | S | Cl | F | $CO_2CH_3$ | $n_D^{20} = 1.5912$ |

The following examples illustrate the possibilties for use of the compounds of the invention.

EXAMPLE A

In a greenhouse, the noted plant species were treated post-emergently with the noted compounds of the invention, at a rate of 0.1 kg active ingredient/ha. The compounds of the invention were sprayed evenly over the plants as emulsions in 500 liters water/ha. Three weeks after the treatment the compounds of the invention showed a high crop selectivity with excellent activity against the weeds.

In the following table:
0=no activity
4=total destruction to the plant.
—=not tested
Br=*Brassica* napus napus
Ho=*Hordeum* vulgare
Or=*Oryza* sativa
So=*Solanum* sp.
Ph=*Phaseolus* vulgaris
He=*Helianthus* annuus
Ab=*Abutilon* hybridum
Ma=*Matricaria* chamomilla
Vi=*Viola* tricolor
Ch=*Chrysanthemum* segetum
Ip=*Ipomoea* purpurea
Se=*Setaria* italica
Ga=*Galium* aparine

| Compounds of invention | Br | Ho | Or | So | Ph | He | Ab | Ma | Vi | Ch | Ip | Se | Ga |
|---|---|---|---|---|---|---|---|---|---|---|---|---|---|
| Example 10 | 0 | 0 | 0 | 4 | 4 | 3 | 4 | 3 | 4 | 3 | 3 | 3 | 3 |
| Example 34 | — | 0 | — | — | — | — | 4 | 2 | — | — | 4 | 2 | 3 |
| Example 37 | 0 | 0 | — | — | — | — | 4 | 0 | 3 | — | 3 | — | 2 |
| Example 40 | — | 0 | — | — | — | — | 4 | 3 | — | — | 4 | 3 | 4 |
| Example 41 | — | 1 | — | — | — | — | 4 | 4 | — | — | 4 | 3 | 4 |
| Untreated | 0 | 0 | 0 | 0 | 0 | 0 | 0 | 0 | 0 | 0 | 0 | 0 | 0 |

Similar herbicidal activity was also shown by the compounds of the invention of Examples 1 to 9, 11 to 33, 35, 36, 38, 39 and 42 to 53.

EXAMPLE B

In a greenhouse, the noted plant species were treated post-emergently with the noted compounds of the invention at a rate of 0.1 kg active ingredient/ha. The compounds of the invention were sprayed evenly over the plants as emulsions in 500 liters water/ha. Two weeks after the treatment the compounds(of the invention showed a high crop selectivity in wheat with excellent activity against the weeds. The comparison material did not show a similar high level of activity.

In the following table:
0=no damage
1=1-24% damage
2=25-74% damage
3=75-89% damage
4=90-100% damage
Be=*Beta* vulgaris altissima
Br=*Brassica* sp.
Tr=*Triticum* aestivum
Se=*Setaria* viridis
Ga=*Galium* aparine
Po=*polygonum* sp.
Ve=*Veronica* persica
Vi=*Viola* sp.

| Compounds of invention | Tr | Be | Br | Se | Ga | Po | Ve | Vi |
|---|---|---|---|---|---|---|---|---|
| Example 35 | 0 | 4 | 4 | 3 | 4 | 4 | 4 | 4 |
| Example 47 | 0 | 4 | 4 | 4 | 4 | 4 | 4 | 4 |
| Example 51 | 0 | 4 | 4 | 3 | 4 | 4 | 4 | 4 |
| Untreated | 0 | 0 | 0 | 0 | 0 | 0 | 0 | 0 |
| Comparison material | | | | | | | | |
| Ioxynil | 0 | 4 | 3 | 0 | 0 | 2 | 3 | 2 |

EXAMPLE C

In a greenhouse, the noted plant species were treated post-emergently with the noted compounds of the invention at a rate of 0.3 kg active ingredient/ha. The compounds of the invention were sprayed evenly over the plants as emulsions in 500 liters water/ha. Two weeks after the treatment the compounds of the invention showed a high crop selectivity in maize with excellent activity against the weeds. The comparison material did not show a similar high level of activity. In the following table:
0=no damage
1=1-24% damage
2=25-74% damage
3=75-89% damage
4=90-100% damage
—=not tested
Ze=*Zea* mays Be = *Be*ta vulgaris altissima
Br = *Br*assica sp.
Gl = *Gl*ycine maxima
Go = *Go*ssypium hirsutum
He = *He*lianthus annuus
Se = *Se*taria viridis
Ab = *Ab*utilon theophrasti
Ga = *Ga*lium aparine
Ip = *Ip*omoea purpurea
Ma = *Ma*tricaria chamomilla
Po = *Po*lygonum sp.
Sb = *Sb*esbania exaltata
So = *So*lanum sp.
Ve = *Ve*ronica
Vi = *Vi*ola sp.

| Compounds of invention | Ze | Be | Br | Gl | Go | He | Se | Ab | Ga | Ip | Ma | Po | Sb | So | Ve | Vi |
|---|---|---|---|---|---|---|---|---|---|---|---|---|---|---|---|---|
| Example 34 | 0 | 3 | 4 | 3 | 3 | 1 | 3 | 4 | 3 | 4 | 2 | 4 | 4 | 4 | 2 | 3 |
| Example 36 | 0 | 4 | 3 | 2 | 4 | 4 | 3 | 4 | 3 | 4 | 4 | — | — | — | 4 | 3 |
| Example 37 | 1 | 3 | 1 | 1 | 4 | 2 | 2 | 4 | 2 | 3 | 1 | — | — | — | 4 | 3 |
| Example 52 | 0 | 4 | 1 | 0 | 4 | 3 | — | 4 | 3 | 4 | 2 | 1 | 4 | 4 | 4 | 2 |
| Untreated Comparison material | 0 | 0 | 0 | 0 | 0 | 0 | 0 | 0 | 0 | 0 | 0 | 0 | 0 | 0 | 0 | 0 |
| Oxadiazon | 2 | 4 | 4 | 2 | 4 | 2 | 3 | 4 | 4 | 4 | 3 | 4 | 4 | 4 | 4 | 4 |

EXAMPLE D

In a greenhouse, the noted plant species were treated post-emergently with the noted compounds of the invention at a rate of 0.3 kg active ingredient/ha. The compounds of the invention were sprayed evenly over the plants as emulsions in 500 liters water/ha. Two weeks after the treatment the compounds of the invention showed a high crop selectivity In soya with excellent activity against the weeds. The comparison material did not show a similar high level of activity.

In the following table:
0 = no damage
1 = 1-24% damage
2 = 25-74% damage
3 = 75-89% damage
4 = 90-100% damage
Gl = *Gl*ycine maxima
Be = *Be*ta vulgaris altissima
Br = *Br*assica sp.
Go = *Go*ssypium hirsutum
He = *He*lianthus annuus
Ab = *Ab*utilon theophrasti
Ga = *Ga*lium aparine
Ip = *Ip*omoea purpurea
Ma = *Ma*tricaria chamomilla
Po = *Po*lygonum sp.
Se = *Se*sbania exaltata
So = *So*lanum sp.
Ve = *Ve*ronica persica
Vi = *Vi*ola sp.

| Compounds of invention | Gl | Be | Br | Go | He | Ab | Ga | Ip | Ma | Po | Se | So | Ve | Vi |
|---|---|---|---|---|---|---|---|---|---|---|---|---|---|---|
| Example 46 | 1 | 4 | 4 | 4 | 2 | 4 | 3 | 4 | 2 | 2 | 3 | 4 | 4 | 4 |
| Example 48 | 0 | 2 | 3 | 4 | 4 | 4 | 4 | 4 | 2 | 3 | 3 | 4 | 3 | 4 |
| Example 50 | 1 | 2 | 3 | 4 | 1 | 4 | 4 | 3 | 2 | 3 | 2 | 4 | 3 | 4 |
| Example 52 | 0 | 4 | 1 | 4 | 3 | 4 | 3 | 4 | 2 | 1 | 4 | 4 | 4 | 2 |
| Untreated Comparison material | 0 | 0 | 0 | 0 | 0 | 0 | 0 | 0 | 0 | 0 | 0 | 0 | 0 | 0 |
| Oxadiazon | 2 | 4 | 4 | 4 | 2 | 4 | 4 | 4 | 3 | 4 | 4 | 4 | 4 | 4 |

EXAMPLE E

In a greenhouse, the compounds of the invention shown in the table were applied at the rates given. For this the compounds were applied in vessels containing 1500 ml water. As test plants there were used Echinochloa crus-galli, Oryza sativa (Or), Echinochloa crus-galli (Ec), Cyperus difformis (Cy) and Eliocharis acicularis (El) in the 2 to 5 leaved stage. Three weeks after the treatment the compounds of the invention showed strong activity against rice weeds whilst at the same time showing selectivity to paddy rice.

In the following Table:
0 = no damage
1 = 1-24% damage
2 = 25-74% damage
3 = 75-89% damage
4 = 90-100% damage

| Compound of the invention | Water application ppm | Or | Ec | Cy | El |
|---|---|---|---|---|---|
| Example 15 | 10 | — | 4 | 3 | 4 |
| Example 35 | 1 | 0 | 4 | — | — |

Similar herbicidal activity was also shown by the compounds of the invention of Examples 1 to 14, 16 to 34 and 36 to 53.

We claim:
1. An anilino iminoazole or iminoazine of formula I

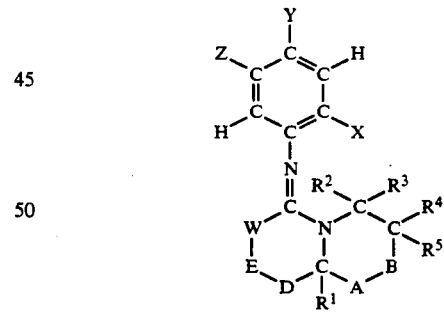

in which
A is the group $(CH_2)_n$,
B is the group $CH_2$,

D is the group $(CH_2)_n$,
E is the group $CR^{12}R^{13}$,
W is or sulphur,
X is halogen and Y is hydrogen or halogen,
Z is hydrogen, trifluoromethyl or one of the groups —$OR^{14}$, —$SR^{14}$, —$NR_2^{14}$ or —$CO_2R^{15}$,
$R^1$ is hydrogen,
$R^2$, $R^3$, $R^4$, $R^5$, $R^{12}$, and $R^{13}$, independently of each other, are hydrogen or $C_1$–$C_4$-alkyl,
$R^{14}$ is hydrogen, a $C_1$–$C_{12}$-alkyl, $C_2$–$C_6$-alkenyl, $C_3$–$C_8$-alkynyl, a $C_1$–$C_4$-alkoxy-carbonylmethyl or $C_1$–$C_4$-alkylsuphonyl,
$R^{15}$ is hydrogen, a $C_1$–$C_6$-alkyl, $C_2$–$C_6$-alkenyl or $C_3$–$C_6$-alkynyl group,
n is 0 or 1,
or their salts with inorganic or organic acids.

2. An anilino iminoazole of formula I

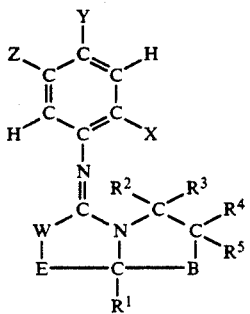

in which
B is the group —$CH_2$—,
E is the group —$CH_2$—,
W is or sulphur,
X and Y, independently of each other, are hydrogen or halogen,
Z is hydrogen, trifluoromethyl or one of the groups —$OR^{14}$, —$SR^{14}$ or —$CO_2R^{15}$,
$R^1$ is hydrogen,
$R^2$, $R^3$, $R^4$ and $R^5$, independently of each other, are hydrogen or $C_1$–$C_4$-alkyl,
$R^{14}$ is hydrogen, a $C_1$–$C_{12}$-alkyl, $C_2$–$C_6$-alkenyl, $C_3$–$C_8$-alkylnyl, $C_1$–$C_4$-alkoxy-carbonylmethyl or $C_1$–$C_4$-alkysulphonyl,
$R^{15}$ is hydrogen, a $C_1$–$C_6$-alkyl, $C_2$–$C_6$-alkenyl or $C_3$–$C_6$-alkynyl group,
or their salts with inorganic or organic acids.

3. Compound according to claim 1 in which n is 0.

4. A compound according to claim 2 in which $R^1$, $R^2$, $R^3$ and $R^5$ are hydrogen, $R^4$ is hydrogen or alkyl, m is 0, X is halogen, Y is halogen, Z is —$OR^{14}$ or —$CO_2R^{15}$, and $R^{14}$ and $R^{15}$, independently of each other, are alkyl or alkynyl.

5. Compound according to claim 4 in which X is fluoro and Y is chloro.

6. Compound according to claim 5 in which $R^4$ is hydrogen or methyl and $R^{14}$ and $R^{15}$, independently of each other, are methyl or ethyl.

7. Compound according to claim 5 in which $R^4$ is hydrogen and W is S.

8. Compound according to claim 5 in which $R^4$ is hydrogen, W is S and Z is $OR^{14}$ in which $R^{14}$ is alkynyl.

9. Compound according to claim 8 in which $R^{14}$ is —$CH_2$—$C\pm CH$.

10. A herbicidal composition which comprises a compound according to claim 1, in admixture with carriers and diluents.

11. A herbicidal composition which comprises a compound according to claim 4, in admixture with carriers and diluents.

12. A herbicidal composition which comprises a compound according to claim 5, in admixture with carriers and diluents.

13. A herbicidal composition which comprises a compound according to claim 8, in admixture with carriers and diluents.

14. A herbicidal composition which comprises a compound according to claim 9, in admixture with carriers and diluents.

15. A herbicidal composition which comprises a compound according to claim 2, in admixture with carries and diluents.

16. A method of combating weeds which comprises applying to the weeds or their locus a compound according to claim 1.

17. A method of combatting weeds which comprises applying to the weeds or their locus a compound according to claim 4.

18. A method of combatting weeds which comprises applying to the weeds or their locus a compound according to claim 5.

19. A method of combatting weeds which comprises applying to the weeds or their locus a compound according to claim 8.

20. A method of combatting weeds which comprises applying to the weeds or their locus a compound according to claim 9.

21. A method of combatting weeds which comprises applying to the weeds or their locus a compound according to claim 2.

* * * * *